United States Patent [19]

Meriläinen

[11] Patent Number: 5,611,348
[45] Date of Patent: Mar. 18, 1997

[54] METHOD OF MEASURING GAS EXCHANGES AND METABOLISM

[75] Inventor: Pekka Meriläinen, Helsinki, Finland

[73] Assignee: Instrumentarium Corp., Finland

[21] Appl. No.: 310,953

[22] Filed: Sep. 23, 1994

[30] Foreign Application Priority Data

Sep. 24, 1993 [FI] Finland ................................. 934211

[51] Int. Cl.$^6$ ................................................ A61B 5/097
[52] U.S. Cl. ........................... 128/719; 128/730; 73/23.3; 422/84
[58] Field of Search ..................... 128/718, 719, 128/730; 422/84; 73/23.3

[56] References Cited

U.S. PATENT DOCUMENTS

| | | |
|---|---|---|
| 4,202,352 | 5/1980 | Osborn . |
| 4,658,832 | 4/1987 | Brugnoli . |
| 4,818,489 | 4/1989 | Gonner et al. ......................... 422/84 |
| 4,856,531 | 8/1989 | Meriläinen . |
| 5,042,501 | 8/1991 | Kenny et al. . |
| 5,117,674 | 6/1992 | Howard . |
| 5,140,993 | 8/1992 | Opekun, Jr. et al. .................. 128/730 |
| 5,425,374 | 6/1995 | Ueda et al. ............................ 128/719 |

FOREIGN PATENT DOCUMENTS

| | | |
|---|---|---|
| 312308 | 4/1989 | European Pat. Off. . |
| 78231 | 3/1989 | Finland . |
| 1915959 | 10/1970 | Germany . |
| 3533557 | 5/1986 | Germany . |
| 7316618 | 2/1975 | Sweden . |

*Primary Examiner*—Lee S. Cohen
*Attorney, Agent, or Firm*—Andrus, Sceales, Starke & Sawall

[57] ABSTRACT

The invention relates to a portable collection container (5) for a test person, and a method for measuring and analyzing the expiration gas collected into the container (5). The container (5) is made of laminate. In the method, the container when discharged by low pressure suction, is folded into its original folded state.

11 Claims, 2 Drawing Sheets

METHOD OF MEASURING GAS EXCHANGES AND METABOLISM

BACKGROUND OF THE INVENTION

The invention relates to a method of measuring gas exchanges and metabolism and collecting the gases and to a container therefor.

There are many devices available for measuring the gas exchanges and the metabolism at rest or during artificial stress. These devices are presently used especially for testing athletes, but also for testing the fitness of others. A device measuring the metabolic quantities can e.g. be connected to a respirator as presented in the U.S. Pat. No. 4,865,531, which by measuring the respiratory exchanges calculates the energy consumption on the basis of oxygen consumption in a certain state of equilibrium and concludes the quality of a nourishment digested on the basis of a ratio of carbon dioxide output to oxygen consumption. This device has almost entirely been used for measuring the respiration of a patient connected to a respirator. A reliable measuring in actual conditions during physical stress and work performances is, however, more of interest to many scientists. Portable devices have been developed, but these have proved technically undependable. Therefore, the scientists still use the so called Douglas-bag-method, characterized in that a timed collection of expired gas is collected into a bag of 1–2 kg with a volume of 100–150 liters, and the volume and the gas contents are analyzed later. In the collecting stage, the test person's nose is closed mechanically, and he breathes through his mouth into the valve system, so that the inhalation comes from the open air and the expiration is lead through a hose to said bag. The system also contains a manually controlled change valve, by which the expiration is directed from the air to the bag in the beginning of the test, and in the reverse direction at the end of the test. The gas collecting time is measured by a clock. The rubberized breathing Douglas-bags are hung from the ceiling during the test, in order not to disturb the test by their weight. The test person does not thus carry the bag, wherefore the state of stress has always to be arranged artificially in places equipped with a bag suspension carrier.

The mouth of the Douglas-bag is made of a different material, generally polyethylene or alike, than the rest of the bag in order to accommodate the valve. The bag can, therefore, only be closed by the valve.

When a required amount of expired air has been collected into the bag, its carbon dioxide and oxygen contents are analyzed. The volume is measured by discharging the bag by pressing manually and by folding e.g. into a gas bell type spirometer (Tissot-spirometer). A small sample of the gas is also taken for measuring the $CO_2$ and $O_2$-contents in gas analyzers.

In the solution according to the U.S. Pat. No. 4,763,664, the patient inhales the gas floating to a dome. The patient's expired air is constantly sucked through a hose to the analyzer to be analyzed, the patient's head being simultaneously in the dome. Such a solution can only be applied to a patient at rest. The volume and shape of the dome do not essentially change during the test.

SUMMARY OF THE INVENTION

The subject invention presents a method and a device which simplifies and expedites the measuring of the gas exchange in field circumstances, and which can be applied in considerably more diversified embodiments and test circumstances than traditional methods and devices. The method according to the invention utilizes the measuring method according to the U.S. Pat. No. 4,856,531 as well as a new type of container connected to the same, which can be used for measuring gas exchanges and metabolism, and which does not necessarily need to be rolled.

The advantages of the invention are i.a. that the test person can carry the container during the test due to its lightness. The mouth of the container is easy to close and to open. The container is easily discharged to its former folded shape. It can easily be connected to most of the analyzing devices, in which the respiratory air is sucked from the container to measure the respiratory air quantities. The same device can be used for measuring the energy consumption both at rest and at stress. The method is more accurate than on-line measurement methods. The container can be stored in very small space.

BRIEF DESCRIPTION OF THE DRAWING

The invention is described more in detail with reference to the drawing, in which.

DESCRIPTION OF THE PREFERRED EMBODIMENT

Figure 1:
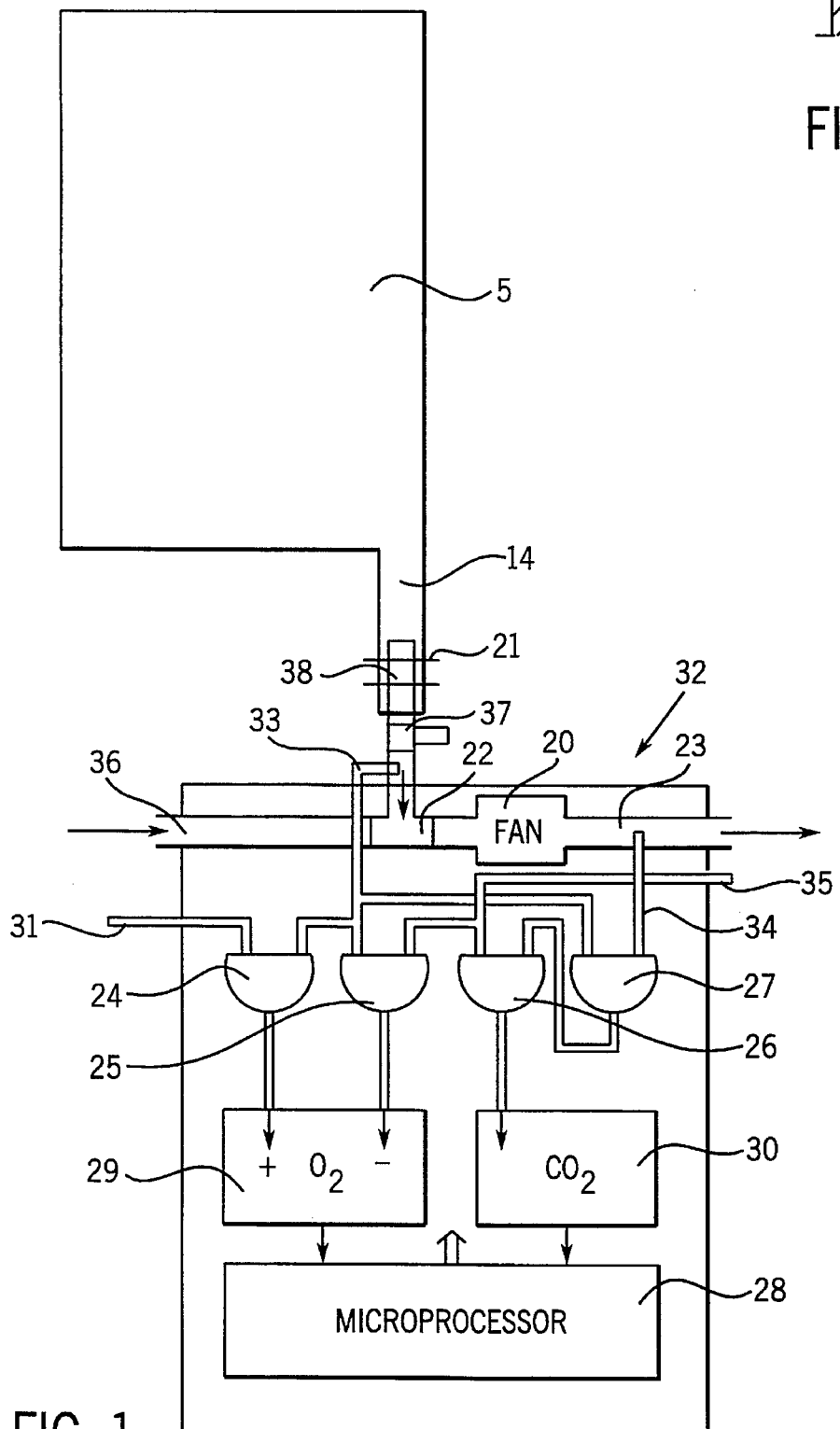
FIG. 1 presents the container and the measuring device

FIG. 1 presents a device for measuring the contents of the expired air when discharging it from the container 5 after the container or bag has been breathed full by the test person. In the method, the air contained in the expired container 5 is sucked by the device 20 generating low pressure, and at the same time the container gradually folds preferably to its former shape during the discharging. In the preferable solution in FIG. 1, the mouth 14 of the container is connected to the aggregate 38 of the measuring device 32 by the fixing element 21. To the T-fitting 22 of the device has been connected a change valve 37 having an outgoing tube 38, on which the mouth 14 is sealed. The expired air sucked from the container 5 as well as the air from outside the container 5 flowing along the tube 36, are mixed in the T-fitting 22 into a constant flow K of typically e.g. 80 l/min. produced by the device 20 generating low pressure. The device holds the constant flow so that the sum of the flow of the gas from the container and the flow of the outside air is kept at said predetermined constant flow. The ratio between these flows can vary. From the change valve 37, which can be attached to the measuring device 32, there is a connection either to the outside of the container 5, generally the open air or to the container.

The carbon dioxide output can be calculated without flow measuring by measuring the carbon dioxide content in the container mouth 14 through the sample hose 33 and in the output hose 23 through the sample hose 34 at a suitable rate alternately or simultaneously by using two carbon dioxide sensors 30, which, however, is not a functional solution in practice.

The oxygen consumption on the other hand can be defined by also measuring the oxygen covalent of the open air and the oxygen content of the mixed expired gas in the bag. A known result for the respiratory quotient is thus obtained by using a known supposition, according to which the nitrogen consumption is zero.

The sucked air goes via the device, in which the quantity of the carbon dioxide and its oxygen deficiency in relation to the indoor air as well as the total volume of the gas are measured according to the dilution principle. The device comprises $O_2$- and $CO_2$-sensors 29, 30 for the measuring. The device generating low pressure, e.g. a suction fan 20, discharges the container 5, and also mixes to the gas in the container in a certain ratio the external air from outside the device. Measuring the gas contents by using the computer controlled magnetic valves 24–27 both before and after the mixing, enables the calculation of required gas volumes using the dilution principle by the following formula:

$$V_{CO2} = \left( K \int_0^T F^*_{ECO2}\, dt \right) / t$$

$$V_{O2} = V_{CO2}/RQ$$

in which K equals the flow constant, t is the collection time of the container, T is the discharging time of the container, $F_{ECO2}$ is the carbon dioxide content measured in the hose 23, RQ is the respiratory quotient, $V_{CO2}$ is the carbon dioxide output and $V_{O2}$ is the oxygen consumption.

The measuring of the gas contents in different measuring points through the sample hoses 31, 33, 34, 35, is realized periodically by the magnetic valves 24–27 controlled by the microprocessor 28. The tubes 31, 35 are for measuring the oxygen and the carbon dioxide contents of the air outside the container 5 or the device 32.

The final result of the average oxygen consumption and carbon dioxide output of the test person during the test is received by dividing the obtained gas volumes with the gas collection time measured during the test.

The dome described in the U.S. Pat. No. 4,763,664 can also be connected to the measuring device for measuring the reference value of the test person at rest. The dome comprises preferably a clear, essentially semi-ellipsoid-shaped chamber with a plastic film skirt air-tightly fained to its edges, which skirt can be folded tightly under the patient's head, as well as hose connectors connected to the same with related flow diffusers. The suction fan can suck indoor air to the device through the dome. Thereby, the test person's rest energy consumption required as reference value can easily be measured by the same device by connecting to it the said dome with a hose, and using for the calculations an appropriate computer program.

As the carbon dioxide sensor 30 can be used e.g. an analyzer based on $CO_2$ infrared absorption, and as the oxygen sensor 29 e.g. a fast differential paramagnetic oxygen sensor, which also provide the means of using a fast measuring sequence.

Preferably, the container 5 used in the above method can be made of e.g. laminate. The laminate comprises two films 1, 3, of which one is metallised, e.g. with aluminum. The films are bonded to a laminate so that the metallisation 2 is between the two films. These films as bonded form the wall of the container. The films are of material that can be heat-sealed, e.g. polyolefin (orientated polypropylene) or e.g. PE-lacquer, or material with corresponding properties. When the thickness of the aluminum foil is approx. 1–3, preferably 2 µm, and the thicknesses of the films approx. 10–100 µm, the weights of the containers are typically approx. 50–300 g, preferably 50–200 g, and more preferably 70–150 g, the volume of the expired gas collection container being typically below approx. 200 l, preferably 100–150 l.

Containers of this weight can be carried by the test person without disturbing the test. With the above mentioned thicknesses of the metallised orientated polypropylene films, the diffusion ratios measured according to the DIN-53380 method in the unit $cm^3/(m^2\ d\ bar)$ are with oxygen 200, preferably below 300 and with carbon dioxide 600 preferably below 700, which are more than 7 times smaller than with a mere orientated polypropylene. The wall material is preferably made of essentially non-resilient material.

Figure 4:
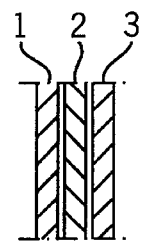
FIG. 4 shows schematically a cross section of the wall material of the container.
Figure 2:
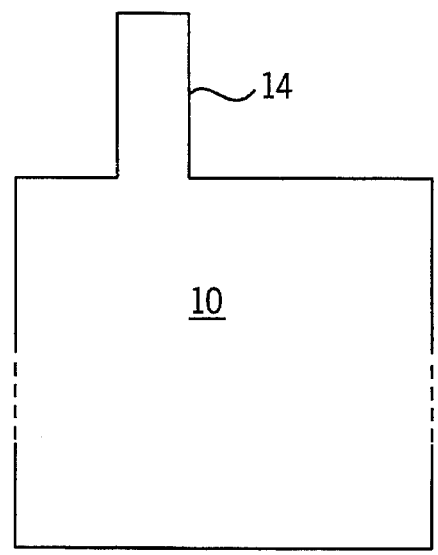
FIG. 2 presents one blank of the container
Figures 3A, 3B:
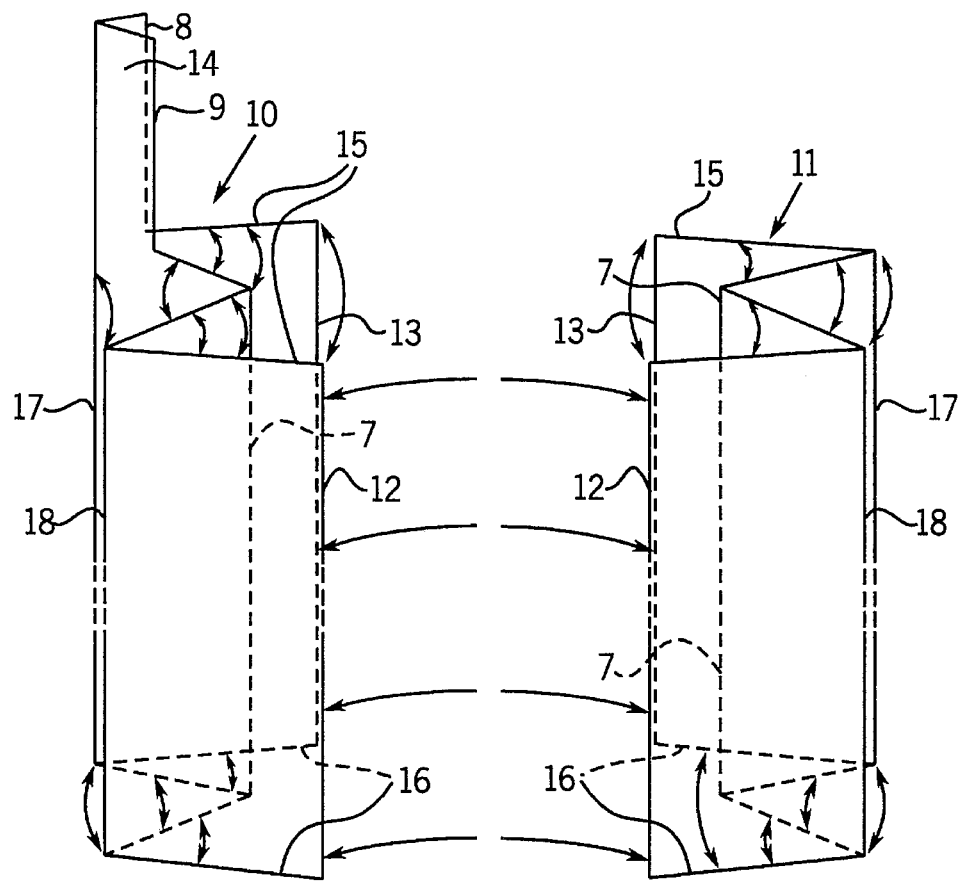
FIGS. 3A and 3B present two blanks to be attached to each other

Another important factor besides the weight is, that the bag used as container can be folded into a small space, and that it also folds to its former shape when discharged. The FIGS. 2, 3 and 4 present the manufacture of a preferably shaped bag for the collecting container of the invention. The pictures show the use of two blanks, but the bag can also be made of one single blank. FIGS. 3A and 3B show by dotted lines the portions that remain behind the blank. The arrow lines show the sides to be heat-sealed. In FIG. 3A, the blank 10, containing the blank for the mouth 14, is spread out. There are two blanks 10 and 11, one of them containing also the mouth of the bag. The blanks are first folded double so that the longitudinal sides come against each other. The closed sides 7 of the blanks are folded in the middle inward, forming the folded lines 17, 18. The ends 12 and 13 of the blanks coming against each other are heat-sealed together as also the gable seams 15 and 16 in the horizontal directions. The mouth 14 of the bag is longitudinally heat-sealed all the way to the gable seem 15. To minimize the expiration task of the test person, the diameter of the mouth 14 can be e.g. approx. 20–40 mm, preferably approx. 30 mm or bigger, so that its walls do not cause excessive resistance, which could influence the measuring result. The mouth 14 of the bag can be closed by a clamp e.g. by folding double the mouth of the hose or a portion of it, and preferably by pressing a clamp to this portion. As shown in FIGS. 3A and 3B, the hose-shaped portion being one piece with the bag, can preferably serve as the mouth. A reinforcing hose can be stuck into the mouth if required to keep the hose-shaped portion open. The mouth is preferably folded to an extension of the folded line 17 or 18, by which the mouth is essentially divided into two portions of equal size, the free edges 8, 9 of which are seamed together.

Straps can be attached to the container to project longitudinally outward from the container either fixedly attached to the container or e.g. by adhesive fixing. These can be of the same piece with the rest of the container.

The analyzing of the respiratory air is thus made by measuring the respiratory air contents both at rest and at stress, and based on these measures calculating the gas exchange and metabolic rate quantities, carbon dioxide output and oxygen consumption as well as their ratios at rest and at stress.

The invention has above been described with reference to one of its preferable embodiments. The invention should not, however, be considered as so limited, but all modifications within the scope of the inventive idea defined by claims are possible.

I claim:

1. A method for measuring a desired property of the respiratory gas of a patient, said method comprising the steps of:

collecting gas expired by the patient into a gas tight, closable container;

closing the container after the expired gas has been collected;

connecting the container to a measuring device and thereafter opening the container;

creating a low pressure in the measuring device in fluid communication with the container and with ambient air;

sucking the collected expired gas out of the container into the device as a continuous stream of gas with the low pressure;

sucking ambient air into the device as a continuous stream of ambient air with the low pressure;

mixing all of the continuous stream of collected expired gas from the container with the continuous stream of ambient air as the gas and air are sucked into the device and forming a unidirectional gas stream from the gas-air mixture which continuously flows through the device;

ascertaining a selected property of at least one of the expired gas and the gas stream; and measuring, from the foregoing ascertainment, the desired property of the respiratory gas of the patient.

2. A method according to claim 1 wherein the step of forming a gas stream is further defined as forming a constant flow rate gas stream in the device.

3. A method according to claim 2 wherein the ascertaining step is further defined as ascertaining at least one of oxygen and carbon dioxide properties and wherein the measuring step is further defined as measuring a selected one of the oxygen and carbon dioxide contents of the respiratory gas of the patient.

4. A method according to claim 1 wherein the ascertaining step is further defined as ascertaining at least one of oxygen and carbon dioxide properties and wherein the measuring step is further defined as measuring a selected one of the oxygen and carbon dioxide contents of the respiratory gas of the patient.

5. A method according to claim 4 wherein the ascertaining step is further defined as ascertaining volumetric properties and wherein the measuring step is further defined as measuring the volume of gas in the container.

6. A method according to claim 5 wherein the ascertaining step is still further defined as ascertaining the carbon dioxide output and oxygen consumption properties of the respiratory gas of the patient when the patient is at rest, and wherein the measuring step is further defined as calculating the ratio of the properties of the expired gas in the container and the respiratory gas of the patient at rest.

7. A method according to claim 1 wherein the ascertaining step is further defined as ascertaining volumetric properties and wherein the measuring step is further defined as measuring the volume of gas in the container.

8. A method according to claim 1 wherein the step of collecting the expired gas is further defined as expanding a flexible, gas-tight, closable container.

9. A method according to claim 1 wherein the step of sucking the expired gas out of the container is further defined as collapsing a flexible, gas-tight, closable container.

10. A method according to claim 1 wherein the step of collecting the expired gas is further defined as collecting the expired gas when the patient is undergoing exertion.

11. A method according to claim 1 wherein the step of collecting the expired gas is further defined as collecting the expired gas in a portable container.

* * * * *